United States Patent [19]

Martin et al.

[11] Patent Number: 4,705,801
[45] Date of Patent: Nov. 10, 1987

[54] PRODUCTION FOR PRODUCING 3-CYANO-4-PHENYL INDOLES AND INTERMEDIATES

[75] Inventors: Pierre Martin, Rheinfelden; Robert W. Lang, Pratteln, both of Switzerland

[73] Assignee: Ciba-Geigy Corporation, Ardsley, N.Y.

[21] Appl. No.: 784,984

[22] Filed: Oct. 7, 1985

[30] Foreign Application Priority Data

Oct. 16, 1984 [CH] Switzerland ............... 4950/84

[51] Int. Cl.$^4$ ............... A01N 43/36; C07D 207/33; C07D 207/34; C07B 43/08
[52] U.S. Cl. ............... 514/423; 548/560; 548/561; 548/562; 568/308; 568/319; 568/663; 514/427
[58] Field of Search ............... 548/560, 562; 514/423, 514/427

[56] References Cited

U.S. PATENT DOCUMENTS 4,198,502 4/1980 Tarzia ............... 548/539
4,212,806 7/1980 Tarzia .

FOREIGN PATENT DOCUMENTS 2927480 1/1980 Fed. Rep. of Germany .

OTHER PUBLICATIONS

Tetraheiron Letters No. 52, pp. 5337–5340, (1972)—Van Leusen et al.
Synthesis (1976) pp. 281–304—Patterson.
Chem. Ber. 94, p. 676—Wittig et al. (1960).
Helvetica Chimica Acta—vol. 65, Fasc 6 (1982), No. 165—Berney.
Helvetica Chimica Acta—vol. 65, Fasc. 1 (1982) No. 42 Lang et al.

Primary Examiner—Mark L. Berch
Attorney, Agent, or Firm—Edward McC. Roberts; Kevin T. Mansfield

[57] ABSTRACT

There is described a process for producing fungicidally active 4-phenylpyrrole derivatives of the formula I

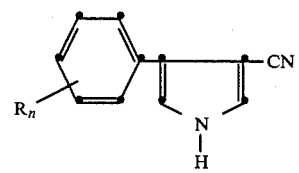

(I)

wherein R is halogen, $C_1$–$C_6$-alkyl or $C_1$–$C_6$-haloalkyl, and n is 0, 1 or 2, which process comprises reacting a 3-trifluoromethyl-4-phenylpyrrole of the formula II

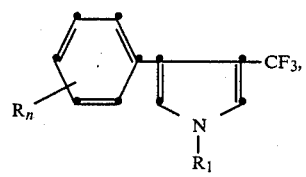

(II)

wherein $R_n$ is as defined under the formula I, and $R_1$ is hydrogen or an acyl group, at elevated temperature and elevated pressure, with ammonia. Important intermediates and the production thereof are also described.

4 Claims, No Drawings

PRODUCTION FOR PRODUCING 3-CYANO-4-PHENYL INDOLES AND INTERMEDIATES

The present invention relates to a novel process for producing 4-phenylpyrrole derivatives of the formula I

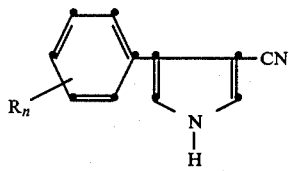

(I)

wherein
R is halogen, $C_1$-$C_6$-alkyl or $C_1$-$C_6$-haloalkyl, and
n is 0, 1 or 2.

By the term 'alkyl' itself or alkyl as a constituent of another substituent, such as haloalkyl, and so forth, are meant, depending on the given number of carbon atoms, for example the following straight-chain or branched-chain groups: methyl, ethyl, propyl, butyl, pentyl, hexyl, and the like, as well as isomers thereof, for example: isopropyl, isobutyl, tert-butyl, isopentyl, and so forth. The prefix 'halo' in the designation of a substituent signifies, here and in the following, that this substituent can occur mono- to perhalogenated. Halogen and halo represent in particular fluorine, chlorine or bromine. Haloalkyl hence denotes a mono- to perhalogenated alkyl group, such as: $CHCl_2$, $CH_2F$, $CCl_3$, $CH_2Cl$, $CHF_2$, $CH_2CH_2Br$, $C_2Cl_5$, $CHBr_2$, $CHBrCl$, and so forth, preferably $CF_3$.

4-Phenylpyrrole derivatives of the formula I wherein n is 0, 1 or 2, and the pyrrole nitrogen is unsubstituted or substituted by acetyl, are known from the German Offenlegungsschrift No. DE-OS No. 2,927,480[1] as plant fungicides.

In the German Offenlegungsschrift No. 2,927,480[1], there is mentioned a process for producing 4-phenyl-3-cyanopyrrole derivatives, which is known from Tetrahedron Letters No. 52, pp. 5337-5340, 1972[2]. In this process, known as the TosMIC process, a cinnamic acid nitrile of the formula X

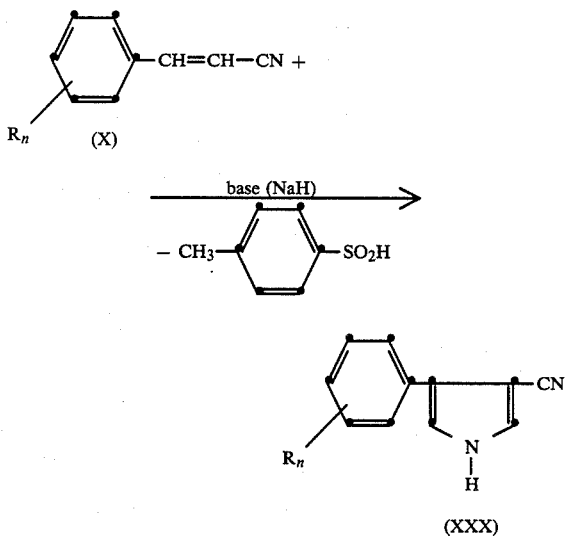

is cyclised with tosylmethylisocyanide (XX) [TosMIC], in the presence of a strong base, for example sodium hydride, to 4-phenyl-3-cyanopyrrole derivatives of the formula (XXX), the symbol R having the meanings defined under the formula I, and n being 0, 1 or 2.

Although a great number of pyrrole syntheses are known (cf. J. M. Patterson, Synthesis, 1976, pp. 281-304[3]), only the TosMIC process outlined above has hitherto resulted directly in the fungicidally valuable 4-phenyl-3-cyanopyrrole derivatives unsubstituted in the 2- and 5-positions. Nevertheless, there is stated in reference (2), with respect to the production of the starting material, 4-phenyl-3-cyanopyrrole, the yield of 35%, which is low for commercial purposes. It has also been shown that the reagent TosMIC has serious disadvantages for commercial syntheses. Thus, TosMIC is subject at elevated temperature, especially above 90° C. (customary drying conditions), to explosive decomposition. On the other hand, residual moisture uses up a portion of the employed base (risk of hydrolysis/reduction in yield). Furthermore, TosMIC has physiological disadvantages, such as irritation to the eyes and skin.

As a result of the disadvantages mentioned, the in itself useful laboratory process is unsuitable for the industrial production of 4-phenylpyrrole derivatives.

There has now been found a novel, more economical and ecologically more favourable process, by which are obtained surprisingly high yields.

The novel process according to the invention for producing the 4-phenylpyrrole derivatives of the formula I defined at the beginning of the text comprises reacting a 3-trifluoromethyl-4-phenylpyrrole of the formula II

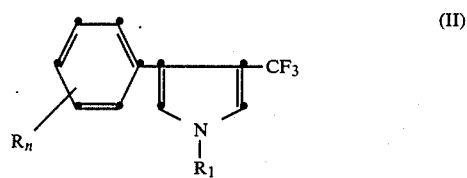

(II)

wherein
R is halogen, $C_1$-$C_6$-alkyl or $C_1$-$C_6$-haloalkyl,
n is 0, 1 or 2, and
$R_1$ is hydrogen or acyl, preferably the group $C(O)R_2$, in which $R_2$ is $C_1$-$C_6$-alkyl, $C_1$-$C_6$-haloalkyl, phenyl or $C_1$-$C_6$-alkoxy,
at elevated temperature and elevated pressure, with ammonia.

Suitable acyl groups are in general all arylcarbonyl, aralkylcarbonyl, alkylcarbonyl and alkoxycarbonyl groups which are unsubstituted or substituted by customary substituents (such as: halogen, cyano, lower alkoxy, lower alkylthio, lower haloalkyl or nitro).

Surprisingly in this reaction, the trifluoromethyl group in the 3-position of the pyrrole ring is converted into a cyano group, and simultaneously the acyl group on the pyrrole nitrogen ($R_1$=acyl, preferably $C(O)R_2$)

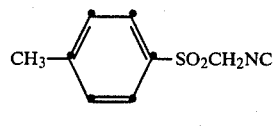

(XX)

is cleaved off, so that there are directly obtained the fungicidally active 4-phenylpyrrole derivatives mentioned in reference (1), which, so far as N-acetylated derivatives are desired, can be subsequently acetylated in the customary manner, for example according to reference (1).

The reaction according to the invention is advantageously performed at temperatures of between room temperature and +230° C., particularly between +160° C. and +200° C.

The reaction is preferably performed in a solvent or solvent mixture inert to the reactants. Suitable solvents are for example: aliphatic and aromatic hydrocarbons, such as benzene, toluene, xylenes, petroleum ether, and so forth; ethers and ethereal compounds, such as dialkyl ether (diethyl ether, diisopropyl ether, tert-butylmethyl ether, and the like), anisole, and especially cyclic ethers, such as dioxane or tetrahydrofuran; alcohols, such as alkanols (methanol, ethanol, propanols, butanols, and so forth), and water, and also mixtures of such solvents with one another.

The pressure range suitable for this reaction is between 1 and 200 bar; with the present of water preferably between 1 and 50 bar; with the absence of water preferably between 40 and 150 bar.

In a preferred embodiment, there is used aqueous ammonia, preferably a concentrated aqueous ammonia solution (about 25 to 34 percent by weight of $NH_3$) in dioxane or tetrahydrofuran. The ammonia can however be produced in the reaction mixture, for example from an ammonium salt, for example an ammonium halide ($NH_4Cl$) and a base (for example NaOH).

The ammonia is generally used in excess, at least however in equimolar amounts; and the reaction is performed in customary pressure vessels, for example bomb tubes, autoclaves, etc.).

A particularly preferred embodiment comprises reacting 3-trifluoromethyl-4-(2,3-dichlorophenyl)pyrrole, or a derivative thereof N-acylated by $C(O)R_2$, wherein $R_2$ has the meanings defined under the formula II, at +50° to +230° C., preferably +160° to +200° C., with excess aqueous ammonia in a cyclic ether, preferably dioxane or tetrahydrofuran, and in a closed pressure vessel, to obtain 3-cyano-4-(2,3-dichlorophenyl)pyrrole.

The starting materials of the formula II are novel: they are plainly predestined, by virtue of the conversion according to the invention of $CF_3$ into CN, to be used as starting products for producing the compounds of the formula I. They have valuable fungicidal properties and likewise form subject matter of the present invention. The compounds of the formula II can be produced for example by reacting a benzaldehyde of the formula III

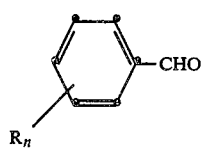

(III)

with an organyloxymethyl-triphenylphosphonium halide of the formula IV

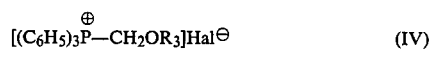

(IV)

to a styrene derivative of the formula V

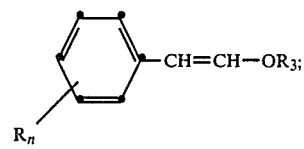

(V)

acetylating this, in the presence of a base, with trifluoroacetic anhydride to a compound of the formula VI

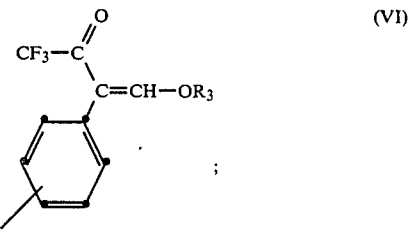

(VI)

cyclising (VI) with an alkali glycinate, preferably a sodium or potassium glycinate, in a carboxylic anhydride of the formula VII $$O[C(O)R_2]_2 \qquad (VII)$$

to an N-acylated 3-trifluoromethyl-4-phenylpyrrole of the formula II'

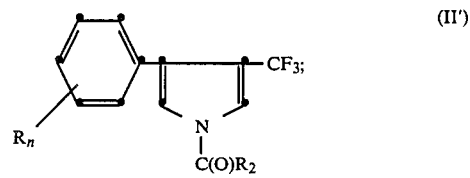

(II')

and, if desired, cleaving off basically the acyl group $C(O)R_3$, so that there is formed a free 3-trifluoromethyl-4-phenylpyrrole of the formula II''

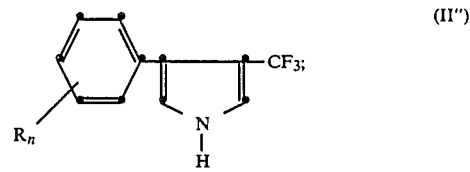

(II'')

$R_n$ in the formulae III, V, VI, II' and II'' and $R_2$ in the formulae VII and II' having the meanings defined under the formula I, $R_3$ in the formula IV being an organyl radical, preferably an aromatic or aliphatic radical, particularly $C_1$–$C_{12}$-alkyl, aralkyl or phenyl, especially $C_1$–$C_6$-alkyl, which is unsubstituted or substituted by customary radicals, and Hal in the formula IV being halogen, preferably chlorine, bromine or iodine.

The described process for producing the compounds of the formula II constitutes a part of this invention.

The reaction of the benzaldehyde III with the organyloxymethyl-triphenylphosphonium halide IV to styrene derivatives of the formula V can be performed analogously to the reactions described in Chem. Ber. 94, 1373 (1961), and is described explicitly in the following by way of an example.

The benzaldehydes of the formula III, the organyloxymethyl-triphenylphosphonium halides of the formula IV and also the anhydrides of the formula VII are in general known, and can be produced in a manner analogous to that for obtaining the known representatives.

The trifluoroacetylation of the styrenes V to give compounds of the formula VI is however novel. It results in high yields but, contrary to customary acetylation reactions, only with the exclusion of solvents, at a temperature of between about +20° and +150° C., preferably between +80° and +120° C., and under elevated pressure. The reaction is generally performed with equimolar amounts of trifluoroacetic anhydride, or advantageously with an excess thereof, in a bomb tube, in an autoclave or in some other pressure vessel. The use of acid-free trifluoroacetic anhydride is of advantage. The bases in this reaction can be organic or inorganic, and they are preferably used in an equimolar amount. Suitable bases are for example inorganic bases, such as the oxides, hydrides, carbonates and carboxylic acid salts of alkaline-earth metals, preferably of alkali metals, especially of sodium and potassium [for example: NaH, Na$_2$CO$_3$, K$_2$CO$_3$, CaCO$_3$, CH$_3$COONa, C$_2$H$_5$COOK, etc.]. Applicable organic bases are trialkylamines, for example triethylamine, piperidine and in particular pyridine bases, such as free pyridine. Since the reaction of (V) to (VI) is novel, resulting in direct precursors (VI) of the fungicidally active compounds of the formulae II' and II'', it forms an important component of the present invention. In the same way, the compounds of the formula VI as direct intermediates for the fungicidally active compounds of the formulae II' and II'' likewise form subject matter of the present invention.

The reaction of the compound of the formula VI with an alkali glycinate and the carboxylic anhydride VII can either be performed by the single-vessel process, wherein all three reactants (VI+glycinate+VII) are simultaneously present, compounds of the formula II' being obtained directly in this manner, or be performed by firstly reacting (VI) with the glycinate to give an intermediate VIII capable of being isolated

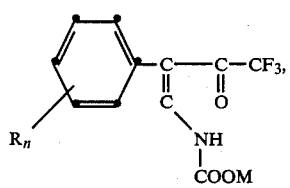
(VIII)

wherein R$_n$ has the meaning defined under the formula I, and M is an alkali metal atom, especially potassium or sodium, and subsequently cyclising (VIII), by reaction with the carboxylic anhydride VII, to obtain compounds of the formula II. Pyrrole syntheses of this type are known from the literature [cf. Helv. Chem. Acta. 65, 1694 (1982)], and can be carried out by methods analogous to those described therein.

Compounds of the formula II'' are produced from compounds of the formula II' by basic cleavage of the acyl group C(O)R$_2$. This basic cleavage can be effected completely analogously to protective-group cleavages known from the literature [cf. Hel. Chem. Acta 65, 407 and 1694 (1982)]. The reaction is generally performed at temperatures of between −20° and +100° C. in customary organic solvents inert to the reactants, and the base used can be one of the organic or inorganic bases mentioned in the foregoing, preferably lithium aluminium hydride.

PRODUCTION OF THE PRECURSORS

Example P1

Production of

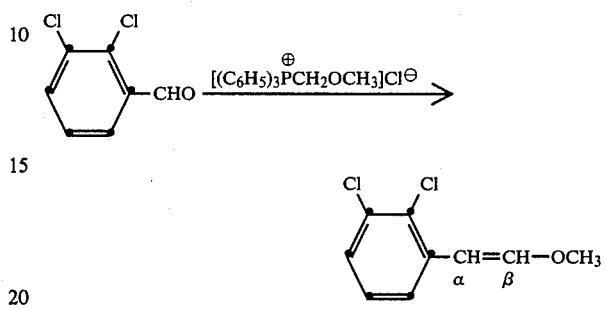

β-Methoxy-2,3-dichlorostyrene 47.3 g of sodium methylate are introduced into 1.5 liters of absolute ethanol. There are then added portionwise, at room temperature, firstly 300.0 g of methoxymethyltriphenylphosphonium chloride and afterwards 142.5 g of 2,3-dichlorobenzaldehyde, and the reaction mixture is heated at 70° C. for about 60 hours. After cooling to room temperature, the mixture is filtered, and the filtrate is concentrated in vacuo. The residue is taken up in pentane, washed, again concentrated by evaporation, and filtered over SiO$_2$ with dichloromethane. Excess solvent is removed in vacuo. There is thus obtained β-methoxy-2,3-dichlorostyrene as a 1:1 (E/Z) mixture in the form of a light-yellow oil.

Example P2

Production of

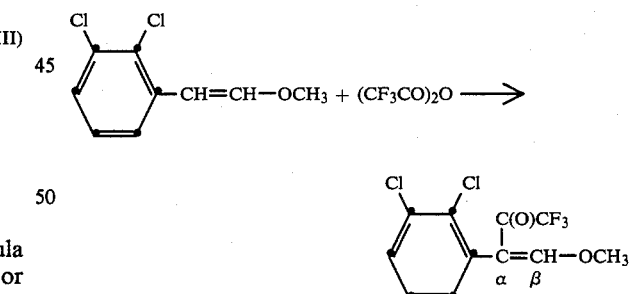

α-Trifluoroacetyl-β-methoxy-2,3-dichlorostyrene 6.1 g of pyridine are added in a bomb tube to 13.5 g of the β-methoxy-2,3-dichlorostyrene produced above. To this mixture are added dropwise, in an argon gas protective atmosphere and with cooling, 24.4 g of trifluoroacetic anhydride. The bomb tube is sealed, and heated at 100° C. for 4 hours. After cooling to room temperature, the reaction mixture is taken up in dichloromethane, and filtered through SiO$_2$. The solvent is evaporated off to thus obtain α-trifluoroacetyl-β-methoxy-2,3-dichlorostyrene as yellow oil.

Example P3

Production of

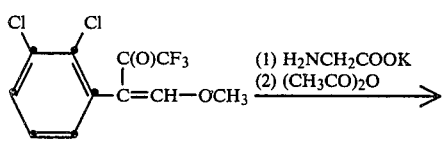

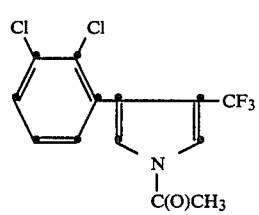

N-Acetyl-4-(2,3-dichlorophenyl)-3-trifluoromethylpyrrole 2.7 g of glycine and 2.0 g of potassium hydroxide are dissolved in 160 ml of ethanol, and the mixture is heated to 45° C. There are then added at this temperature 9.9 g of the α-trifluoroacetyl-β-methoxy-2,3-dichlorostyrene produced according to Example P2, and the reaction mixture is refluxed for 90 minutes. The mixture is subsequently concentrated in vacuo; to the residue are afterwards added 150 ml of acetic anhydride, and the new mixture is heated at 100° C. for 45 minutes. After the evolution of $CO_2$ has subsided, the solvent is removed by evaporation, and the residue is taken up in toluene, and filtered through $SiO_2$. The filtrate is again concentrated by evaporation, and the oily residue is covered with hexane, in the course of which N-acetyl-4-(2,3-dichlorophenyl)-3-trifluoromethylpyrrole precipitates in the form of beige crystals, m.p. 65°–66° C.

Example P4

Production of

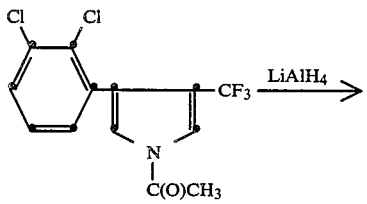

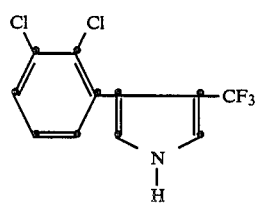

3-Trifluoromethyl-4-(2,3-dichlorophenyl)-pyrrole 29.0 g of N-acetyl-4-(2,3-dichlorophenyl)-3-trifluoromethylpyrrole are dissolved in 500 ml of diethyl ether. This solution is subsequently cooled to 0° C., and to it are added portionwise 13.7 g of lithium aluminium hydride. The mixture is afterwards stirred for 1 hour, and there are then added dropwise at 5° C. 55 ml of 4% sodium hydroxide solution, in the course of which elementary hydrogen is given off, and the mixture is subsequently stirred for a further hour at room temperature. The mixture is then filtered; the filtrate is dried over magnesium sulfate, again filtered, and concentrated by evaporation. The resulting oil is distilled at 150°/8×10$^{-5}$ mbar. By covering it with hexane, there is obtained from the distillate 3-trifluoromethyl-4-(2,3-dichlorophenyl)pyrrole in the form of colourless crystals, m.p. 63°–65° C.

By procedures analogous to those described in the foregoing, there are also obtained the following representatives of compounds of the formula VI, which are typical for the present ivention,

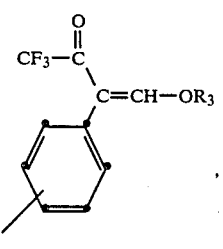

the compounds being obtained in general in the form of 1:1 (E/Z) mixtures.

| Comp. No. | $R_n$ | $R_3$ |
|---|---|---|
| 1.1 | H | $CH_3$ |
| 1.2 | H | $C_3H_7$-n |
| 1.3 | 3-Cl | $CH_3$ |
| 1.4 | 2-Br | $CH_3$ |
| 1.5 | 2,5-$Cl_2$ | $CH_3$ |
| 1.6 | 2,3-$Cl_2$ | $CH_3$ |
| 1.7 | 2-Cl | $CH_3$ |
| 1.8 | 3-$CF_3$ | $CH_3$ |
| 1.9 | 3-Br | $CH_3$ |
| 1.10 | 3-F | $CH_3$ |
| 1.11 | 3-$CH_3$ | $CH_3$ |
| 1.12 | 4-F | $CH_3$ |
| 1.13 | 4-Cl | $CH_3$ |
| 1.14 | 2,4-$Cl_2$ | $CH_3$ |
| 1.15 | 2,3-$Cl_2$ | $C_2H_5$ |
| 1.16 | 2,3-$Cl_2$ | $C_3H_7$-i |
| 1.17 | 2,3-$Cl_2$ | $C_6H_5$ |
| 1.18 | 2-Cl | $C_6H_5$ |

By procedures analogous to those described are obtained also the following representatives of the formula II which are typical for the present invention:

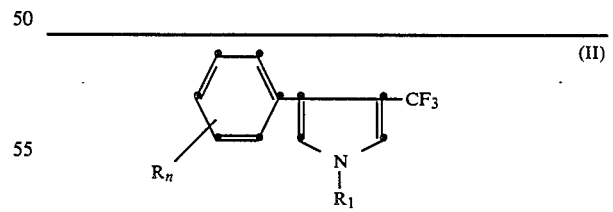

| Comp. No. | $R_n$ | $R_1$ | Physical constants |
|---|---|---|---|
| 2.1 | 2,3-$Cl_2$ | H | m.p. 63–65° C. |
| 2.2 | 2-Br | H | |
| 2.3 | 2,5-$Cl_2$ | H | |
| 2.4 | 2-Cl | H | m.p. 93–94° C. |
| 2.5 | 2-$CF_3$ | H | |
| 2.6 | 3-Br | H | |
| 2.7 | 3-F | H | |
| 2.8 | 3-$CH_3$ | H | |
| 2.9 | 4-F | H | |
| 2.10 | 4-Cl | H | |
| 2.11 | 2,4-$Cl_2$ | H | |

-continued

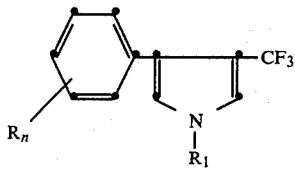

| Comp. No. | $R_n$ | $R_1$ | Physical constants |
|---|---|---|---|
| 2.12 | 3-Cl | H | |
| 2.13 | H | H | |
| 2.14 | 2,3-Cl$_2$ | C(O)CH$_3$ | m.p. 65–66° C. |
| 2.15 | 2-Br | C(O)CH$_3$ | |
| 2.16 | 2,5-Cl$_2$ | C(O)CH$_3$ | |
| 2.17 | 2-Cl | C(O)CH$_3$ | b.p. 130–140°/0,01 mbar |
| 2.18 | 2-CF$_3$ | C(O)CH$_3$ | |
| 2.19 | 3-Br | C(O)CH$_3$ | |
| 2.20 | 3-F | C(O)CH$_3$ | |
| 2.21 | 3-CH$_3$ | C(O)CH$_3$ | |
| 2.22 | 4-F | C(O)CH$_3$ | |
| 2.23 | 4-Cl | C(O)CH$_3$ | |
| 2.24 | 2,4-Cl$_2$ | C(O)CH$_3$ | |
| 2.25 | 3-Cl | C(O)CH$_3$ | |
| 2.26 | 2,3-Cl$_2$ | C(O)CH$_3$ | |
| 2.27 | 2,3-Cl$_2$ | C(O)C$_3$H$_7$—i | |
| 2.28 | 2,3-Cl$_2$ | C(O)C$_6$H$_5$ | |
| 2.29 | 2,3-Cl$_2$ | C(O)OCH$_3$ | |
| 2.30 | 3-Cl | C(O)OC$_2$H$_5$ | |
| 2.31 | 3-Cl | C(O)C$_6$H$_5$ | |
| 2.32 | 3-Cl | C(O)CF$_3$ | |
| 2.33 | 2-Cl | C(O)C$_4$H$_9$—n | |
| 2.34 | 2-Cl | C(O)OC$_3$H$_7$—n | |
| 2.35 | 2-Cl | C(O)C$_2$H$_5$ | |
| 2.36 | 2,3-Cl | C(O)CF$_3$ | |
| 2.37 | H | C(O)CH$_3$ | b.p. 110–120°/0,01 mbar |

The novel pyrrole derivatives of the formula II according to the invention constitute a valuable enlargement of the prior art, for it has been established that the novel pyrroles of the formula II surprisingly exhibit a microbicidal spectrum against phytopathogenic fungi and bacteria which is very favourable for agricultural requirements. They not only can be used in arable farming or in similar fields of application for controlling harmful microorganisms on cultivated plants, but can be additionally used, in the protection of stocks, for preserving perishable goods. Compounds of the formula II have very advantageous curative, systemic and in particular preventive properties, and can be used for the protection of numerous, especially arable, crops. The microorganisms occurring on plants or on parts of plants (fruit, blossom, foliage, stalks, tubers or roots) of various cultivated crops can be inhibited or destroyed with the active substances of the formula II, and also parts of plants subsequently growing remain preserved from such microorganisms.

The active substances are effective for example against the phytopathogenic fungi belonging to the following classes: Ascomycetes, for example Erysiphe, Sclerotinia, Fusarium, Monilinia and Helminthosporium; Basidiomycetes, for example Puccinia, Tilletia and Rhizoctonia; and also against the Oomycetes belonging to the Phycomycetes class, such as Phytophthora. As plant protective agents, the compounds of the formula II can be applied with a particularly high degree of success against important harmful fungi from the Fungi imperfecti family, for example against Cercospora or Piricularia, and especially against Botrytis. Botrytis spp. (B. cinera, B. allii) constitute with botrytis disease on grapevines, strawberries, apples, onions and other fruit and vegetable varieties a significant economic loss factor. Furthermore, some compounds of the formula II can be successfully used for protecting perishable goods of vegetable or animal origin. They combat mould fungi, such as Penicillium, Aspergillus, Rhizopus, Fusarium, Helminthosporium, Nigrospora and Alternaria, as well as bacteria, such as butyric acid bacteria, and yeasts, such as Candida.

As plant protective agents, the compounds of the formula II exhibit, for practical application in agriculture, a very favourable spectrum of activity for protecting cultivated plants, without disadvantageously affecting these by undesirable side effects.

The compounds can also be used as dressing agents for the treatment of seed (fruits, tubers or grain), and of plant cuttings to protect them from fungus infections, and also against phytopathogenic fungi occurring in the soil.

The invention thus relates also to microbicidal compositions, and to the use of the compounds of the formula II for controlling phytopathogenic microorganisms, especially fungi which damage plants, and for preventing an infestation on plants and on provisions of vegetable or animial origin.

In addition, the present invention embraces also the production of (agro)chemical compositions, whereby the active ingredient is intimately mixed with one or more substances or groups of substances described herein. Also included is a process for treating plants or stored provisions, which process comprises the application of the compounds of the formula II, or of the novel compositions, to the plants or parts of plants, or to the locus or the substrate thereof.

Within the scope of this invention, target crops for plant protection are for example the following varieties of plants: cereals (wheat, barley, rye, oats, rice, sorghum and related cereals); beet (sugar beet and fodder beet); pomaceous fruit, stone fruit and soft fruit (apples, pears, plums, peaches, almonds, cherries, strawberries, raspberries and blackberries); legumes (beans, lentils, peas and soya-beans); oil plants (rape, mustard, poppy, olives, sunflowers, coco, castor-oil plants, cocoa and groundnuts); Curcurbitacea (pumpkins, cucumbers and melons); fibre plants (cotton, flax, hemp and jute); citrus fruits (oranges, lemons, grapefruit and mandarins); varieties of vegetables (spinach, lettuce, asparagus, varieties of cabbage, carrots, onions, tomatoes, potatoes and paprika); laurel plants (avocada, cinnamon and camphor); or plants such as maize, tobacco, nuts, coffee, sugar cane, tea, grapevines, hops, bananas and natural rubber plants; and also ornamental plants (composites).

As protective agents for stored products, the compounds of the formula II are used either in an unmodified form or preferably together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, scattering, brushing or pouring, and likewise the type of composition, are selected to suit the objectives to be achieved and the prevailing conditions. Favourable applied amounts are in general 0.01 to at most 2 kg of active ingredient per 100 kg of substrate to be protected; the amounts depend however quite considerably on the nature (extent of surface area, consistency, and moisture content) of the substrate and on enviromental influences thereon.

Within the scope of the present invention, stored stocks and provisions are vegetable and/or animal natural materials and products from further processing, for example the plants which are listed in the following and which have been taken out from the natural life cycle, and parts of these plants (stalks, leaves, tubers, seeds, fruits and grains), the materials being in the freshly harvested condition or in the form resulting from further processing (pre-dried, moistened, crushed, ground or roasted). The following productive materials may be given as examples, which however have no limiting character with respect to the scope of this invention: cereals (such as wheat, barley, rye, oats, rice, sorghum and related cereals); beet (such as carrots, sugar beet and fodder beet); pomaceous fruit, stone fruit and soft fruit (such as apples, pears, plums, peaches, almonds, cherries, strawberries, raspberries and blackberries); legumes (such as beans, lentils, peas and soya-bean); oil plants (such as rape, mustard, poppy, olives, sunflowers, coco, castor-oil plants, cocoa and groundnuts); Cucurbitacea (such as pumpkins, cucumbers and melons); fibre plants (such as cotton, flax, hemp, jute and nettles); citrus fruits; varieties of vegetables (such as spinach, lettuce, asparagus and varieties of cabbage, onions, tomatoes, potatoes and paprika); laurel plants (such as avocada, cinnamon and camphor); or plants such as maize, tobacco, nuts, coffee, sugar cane, tea, grapevines, chestnuts, hops, bananas, grass and hay.

Natural products of animal origin which may be mentioned are in particular dried processed meat and fish products, such as dried meat, dried fish, meat concentrates, bone meal, fish meal and dried animal feed.

By treatment with compounds of the formula II, the treated stored products are lastingly protected against infestation by mould fungi and other undesirable microorganisms. Consequently, the formation of toxic and in part carcinogenic mould fungi (aflatoxines and ochratoxines) is prevented, the material is kept from decomposing, and the quality thereof is maintained high for a prolonged period of time. The process according to the invention can be applied to all dry and moist provisions and stored goods which are susceptible to microorganisms, such as yeasts, bacteria and especially mould fungi.

A preferred process for applying the active substance comprises spraying or wetting the substrate with a liquid preparation, or mixing the substrate with a solid preparation of the active substance. The described conservation process forms a part of the present invention.

Active substances of the formula II are customarily used in the form of compositions, and can be applied, simultaneously or successively, with further active substances to the area or plants to be treated. These further active substances can be fertilisers, trace-element agents or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

Suitable carriers and additives can be solid or liquid and they correspond to the substances customarily employed in formulation practice, for example: natural or regenerated mineral substances, solvents, dispersing agents, wetting agents, adhesives, thickeners, binders or fertilisers.

A preferred method of applying an active substance of the formula II, or an agrochemical composition containing at least one of these active substances, is application to the foliage (leaf application). The number of applications and the amounts applied are governed by the extent of infestation with respect to the pathogen (fungus genus) concerned. The active substances of the formula II can however be fed into the plant through the soil and then by way of the root system (systemic action), this being achieved by the locus of the plant being soaked with a liquid preparation, or by the substances being introduced in solid form into the soil, for example in the form of a granulate (soil application). The compounds of the formula II can also be applied to the seed grains (coating), the grains being for this purpose either soaked with a liquid preparation of the active substance or coated with a solid preparation. Further forms of application are possible in special cases, for example the specific treatment of the stalks or buds of the plants.

The compounds of the formula II are used either in an unmodified form or preferably together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewsie the type of composition, are selected to suit the objectives to be achieved and the given conditions. Favourable applied amounts are in general between 50 g and 5 kg of active substance (AS) per hectare, preferably between 100 g and 2 kg of AS per hectare, and in particular between 200 g and 600 g of AS per hectare.

The formulations, that is to say, the compositions or preparations containing the active substance of the formula II and optionally a solid or liquid additive, are produced in a known manner, for example by the intimate mixing and/or grinding of the active ingredient with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hyrdocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to also add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Particularly advantageous additives facilitating application and rendering possible a marked reduction in the amount of active substance applied are moreover natural (animal or vegetable) or synthetic phospholipids from the class comprising the cephalins and lecithins, for example phosphatidylethanolamine, phosphatidylserine, phosphatidyl glycerol, lysolecithin, plasmalogenes or cardiolipin, which can be obtained for example from animal or plant cells, especially from the brain, heart, liver, egg yokes or soya beans. Applicable commercial mixtures are for example phosphatidylcholine mixtures. Synthetic phospholipids are for example dioctanoylphosphatidylcholine and dipalmitoylphosphatidylcholine.

Depending on the nature of the active ingredient of the formula II to be formulated, suitable surface-active compounds are nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$-$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8-22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the watersoluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide. In the field covering stored provisions, the additives which are preferred are those that are safe for human and animal foodstuffs.

The tensides customarily used in formulation practice are described, inter alia, in the following publications:

"Mc Cutcheon's Detergents and Emulsifiers Annual" MC Publishing Corp., Ridgewood, N.J., 1981; and Dr. Helmut Stache "Tensid-Taschenbuch" (Tenside Handbook) Carl Hanser Verlag, Munic/Vienna, 1981.

The agrochemical preparations contain as a rule 0.1 to 99%, particularly 0.1 to 95%, of active ingredient of the formula II, 99.9 to 1%, especially 99.8 to 5%, of a solid or liquid additive, and 0 to 25%, in particular 0.1 to 25%, of a tenside.

Whereas commercial products are preferably in the form of concentrated compositions, the preparations employed by the end-user are as a rule diluted.

The compositions can contain further additives, such as stabilisers, antifoaming agents, viscosity regulators, binders and adhesives, as well as fertilisers or other active ingredients for obtaining special effects.

Agrochemical compositions of the types described herein likewise form part of the present invention.

The following examples serve to further illustrate the invention without limiting the scope thereof.

PRODUCTION OF THE FINAL PRODUCTS

Example F1

Production of

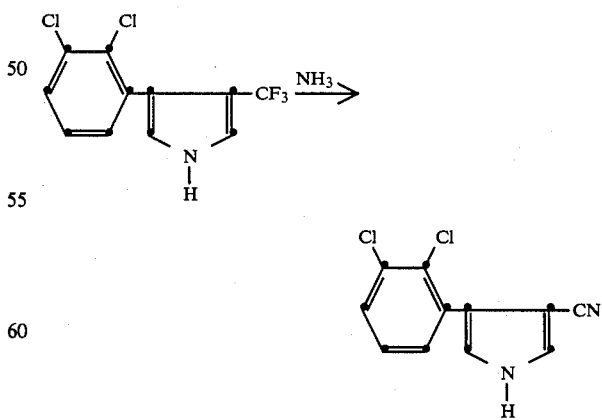

4-(2,3-Dichlorophenyl)-3-cyanopyrrole 4.0 g of 3-trifluoromethyl-4-(2,3-dichlorophenyl)-pyrrole, 21 ml of 25% aqueous ammonia and 40 ml of dioxane are stirred for 26 hours at 180° C. in an autoclave. After cooling to room temperature, the reaction mixture is filtered, and the clear filtrate is concentrated by evaporation. The residue is taken up in ethyl acetate, washed with water and subsequently with diluted sodium chloride solution, dried over magnesium sulfate, filtered, and concentrated by evaporation. The residue is caused to crystallise by the addition of hexane; it is then filtered off and dried to thus obtain 3.4 g (100% of theory) of 4-(2,3-dichlorophenyl)-3-cyanopyrrole having a melting point of 150° C.

Example F2

Production of

4-(2,3-Dichlorophenyl)-3-cyanopyrrole 6.4 g of N-acetyl-4-(2,3-dichlorophenyl)-3-trifluoromethylpyrrole, 15 ml of 25% aqueous ammonia solution and 60 ml of dioxane are stirred for 18 hours at 160° C. in an autoclave. The reaction mixture is cooled to room temperature and filtered, and the clear filtrate is concentrated by evaporation. The viscous residue is dissolved in ethyl acetate; the solution is washed firstly with water and then with a diluted sodium chloride solution; it is subsequently dried over sodium sulfate, filtered, and concentrated by evaporation. To the residue is added n-hexane, and the crystals which precipitate are filtered off and dried. The yield is 5.3 g of 4-(2,3-dichlorophenyl)-3-cyanopyrrole, m.p. 149°–150° C.

By procedures analogous to those described are also obtained the following compounds of the formula I:

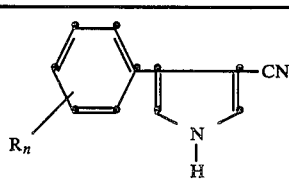

| Comp. No. | $R_n$ | m.p °C. |
|---|---|---|
| 1 | 2,3-Cl$_2$ | 149–150 |
| 2 | 2-Br | 135–138 |
| 3 | 2,5-Cl$_2$ | 137–142 |
| 4 | 2-Cl | 136–138 |
| 5 | 3-CF$_3$ | 87–89 |
| 6 | 3-Br | 132–134 |
| 7 | 3-F | 138–139 |
| 8 | 3-CH$_3$ | 109–111 |
| 9 | 4-F | 137–139 |
| 10 | 4-Cl | 153–155 |

-continued

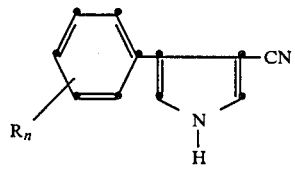

| Comp. No. | $R_n$ | m.p °C. |
|---|---|---|
| 11 | 2,4-Cl$_2$ | 150–152 |
| 12 | 3-Cl | 138–140 |
| 13 | H | 120–123 |

FORMULATION EXAMPLES FOR LIQUID ACTIVE INGREDIENTS OF THE FORMULA II (%=PERCENT BY WEIGHT)

| F1. Emulsion concentrates | (a) | (b) | (c) |
|---|---|---|---|
| active ingredient from the Tables | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| F2. Solutions | (a) | (b) | (c) | (d) |
|---|---|---|---|---|
| active ingredient from the Tables | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |
| (M.W. = molecular weight) | | | | |

The solutions are suitable for application in the form of very fine drops.

| F3. Granulates | (a) | (b) |
|---|---|---|
| active ingredient from the Tables | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4. Dusts | (a) | (b) |
|---|---|---|
| active ingredient from the Tables | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

FORMULATION EXAMPLES FOR SOLID ACTIVE INGREDIENTS OF THE FORMULA II (%=PERCENT BY WEIGHT)

| F5. Wettable powders | (a) | (b) | (c) |
|---|---|---|---|
| active ingredient from the Tables | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with the additives, and the mixture is thoroughly ground in a suitable mill. Wettable powders which can be diluted with water to give suspensions of the required concentration are obtained.

| F6. Emulsion concentrate | |
|---|---|
| active ingredient from the Tables | 10% |
| octylphenol polyethylene glycol ether (4-5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| F7. Dusts | (a) | (b) |
|---|---|---|
| active ingredient from the Tables | 5% | 8% |
| talcum | 95% | — |
| kaolin | — | 92% |

Dusts ready for use are obtained by mixing the active ingredient with the carriers and grinding the mixture in a suitable mill.

| F8. Extruder granulate | |
|---|---|
| active ingredient from the Tables | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| F9. Coated granulate | |
|---|---|
| active ingredient from the Tables | 3% |
| polyethylene glycol (M.W. 200) | 3% |
| kaolin | 94% |
| (M. W. = molecular weight) | |

The finely ground active ingredient is evenly applied in a mixer to the kaolin moistened with polyethylene glycol. Dustfree coated granules are obtained in this manner.

| F.10. Suspension concentrate | |
|---|---|
| active ingredient from the Tables | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained s suspension concentrate from which can be produced, by dilution with water, suspensions of the concentration required.

BIOLOGICAL EXAMPLES

Example B1

Action against *Botrytis cinerea* on beans

Residual-protective action

Bean plants about 10 cm in height are sprayed with a spray liquor prepared from wettable powder of the active ingredient (0.02% of active ingredient). The plants are infested after 48 hours with a conidiospore suspension of the fungus. The extent of fungus infection is assessed after incubation of the infested plants for 3 days at 21° C. with 95-100% relative humidity.

The compounds from the Tables greatly reduce fungus infection not only in the above model test but also in the field test. At a concentration of 0.02%, compounds which prove fully effective (infection 0 to 5%) are for example compounds Nos. 2.1, 2.4, 2.14, 2.17 and 2.37. Infection on untreated but infested bean plants is 100%.

Example B2

Action against *Botrytis cinerea* on apples

Artificially damaged apples are treated by applying drops of spray liquor, prepared from wettable powder of the the active substance, to the damaged areas on the apples. The treated fruit is then inoculated with a spore suspension of *Botrytis cinerea*, and is incubated for one week at about 20° C. with high relative humidity.

For an assessment of the results, the decayed areas of damage are counted, and from the number is deduced the fungicidal action of the test substance. Amongst other effective compounds tested, the compounds Nos. 2.1, 2.4, 2.14, 2.17 and 2.37 completely prevent fungus infection, whereas the level of infection on untreated control fruit is 100%.

What is claimed is:

1. The compound of the formula

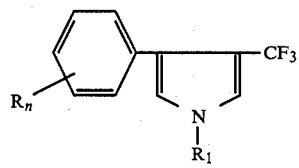

wherein
R is halogen, $C_1$-$C_6$-alkyl or $C_1$-$C_6$-haloalkyl,
n is 0, 1 or 2, and $R_1$ is hydrogen or the group $C(O)R_2$, in which $R_2$ is $C_1$-$C_6$-alkyl, $C_1$-$C_6$-haloalkyl, phenyl or $C_1$-$C_6$-alkoxy.

2. A compound of claim 1, wherein R is chlorine, n is 1 or 2, and $R_1$ has the meanings defined in claim 1.

3. A fungicidal composition comprising an effective amount of a compound of claim 1, together with customary carriers and additives.

4. A process for controlling fungi which damage plants, which process comprises applying to the plants or to the locus thereof a fungicidally effective amount of a compound of claim 1.

* * * * *